(12) United States Patent
Wanders

(10) Patent No.: US 10,039,635 B2
(45) Date of Patent: Aug. 7, 2018

(54) INTRAOCULAR LENS

(71) Applicant: Bernardus Franciscus Maria Wanders, Angerlo (NL)

(72) Inventor: Bernardus Franciscus Maria Wanders, Angerlo (NL)

(73) Assignee: OCULENTIS HOLDING B.V., Eerbeek (NL)

( * ) Notice: Subject to any disclaimer, the term of this patent is extended or adjusted under 35 U.S.C. 154(b) by 760 days.

(21) Appl. No.: 14/370,790

(22) PCT Filed: Jan. 11, 2013

(86) PCT No.: PCT/NL2013/050013
§ 371 (c)(1),
(2) Date: Jul. 7, 2014

(87) PCT Pub. No.: WO2013/105855
PCT Pub. Date: Jul. 18, 2013

(65) Prior Publication Data
US 2015/0005877 A1     Jan. 1, 2015

Related U.S. Application Data

(60) Provisional application No. 61/585,713, filed on Jan. 12, 2012.

(30) Foreign Application Priority Data

Jan. 11, 2012  (NL) ...................................... 2008105

(51) Int. Cl.
*A61F 2/16*     (2006.01)
(52) U.S. Cl.
CPC .......... *A61F 2/1648* (2013.01); *A61F 2/1637* (2013.01)

(58) Field of Classification Search
CPC ..... A61F 2/1648; A61F 2/1637; A61F 2/1618
(Continued)

(56) References Cited

U.S. PATENT DOCUMENTS 4,759,761 A   7/1988 Portnoy
5,217,489 A   6/1993 Van Noy et al.
(Continued)

FOREIGN PATENT DOCUMENTS

EP   0 888 564   1/1999
EP   1 194 797   4/2002
(Continued)

OTHER PUBLICATIONS

International Search Report dated Mar. 18, 2013, corresponding to PCT/NL2013/050013.

*Primary Examiner* — David Isabella
*Assistant Examiner* — Christine Nelson
(74) *Attorney, Agent, or Firm* — Young & Thompson

(57) ABSTRACT

An intraocular lens includes an optic, which includes a first lens having a first optical axis for alignment with an optical axis of the human eye having a macula; and a second lens having a second optical axis. The second optical axis and the first optical axis enclose an angle between 0.5 and 10 degrees. The first and second lens are arranged next to one another in a direction transverse to the first optical axis to provide no overlap in a direction along the first optical axis such that the first lens and the second lens each, independent from one another, image onto the macula of the eye. The angle and a direction of the second optical axis are chosen such that the second lens images onto a functional part of the macula of the human eye, which functional part is not compromised by a defect, such as a scotoma.

16 Claims, 12 Drawing Sheets

(58) Field of Classification Search
USPC .......................................................... 623/6.33
See application file for complete search history.

(56) References Cited

U.S. PATENT DOCUMENTS

| | | | |
|---|---|---|---|
| 5,354,334 | A | 10/1994 | Fedorov et al. |
| 5,507,806 | A * | 4/1996 | Blake .................... A61F 2/1618 264/2.7 |
| 5,699,142 | A | 12/1997 | Lee et al. |
| 6,432,246 | B1 | 8/2002 | Blake |
| 6,536,899 | B1 | 3/2003 | Fiala |
| 8,696,746 | B2 | 4/2014 | Wanders et al. |
| 2007/0182917 | A1 | 8/2007 | Zhang et al. |
| 2007/0276483 | A1 | 11/2007 | Aharoni et al. |
| 2009/0048671 | A1 | 2/2009 | Lipshitz et al. |
| 2012/0029631 | A1 | 2/2012 | Wanders et al. |
| 2014/0172091 | A1 | 6/2014 | Wanders et al. |

FOREIGN PATENT DOCUMENTS

| | | |
|---|---|---|
| EP | 2 219 065 | 8/2010 |
| GB | 2 468 367 | 9/2010 |
| WO | 95/31156 | 11/1995 |
| WO | 2005/055875 | 6/2005 |
| WO | 20101095938 | 8/2010 |
| WO | 20101131955 | 11/2010 |

\* cited by examiner

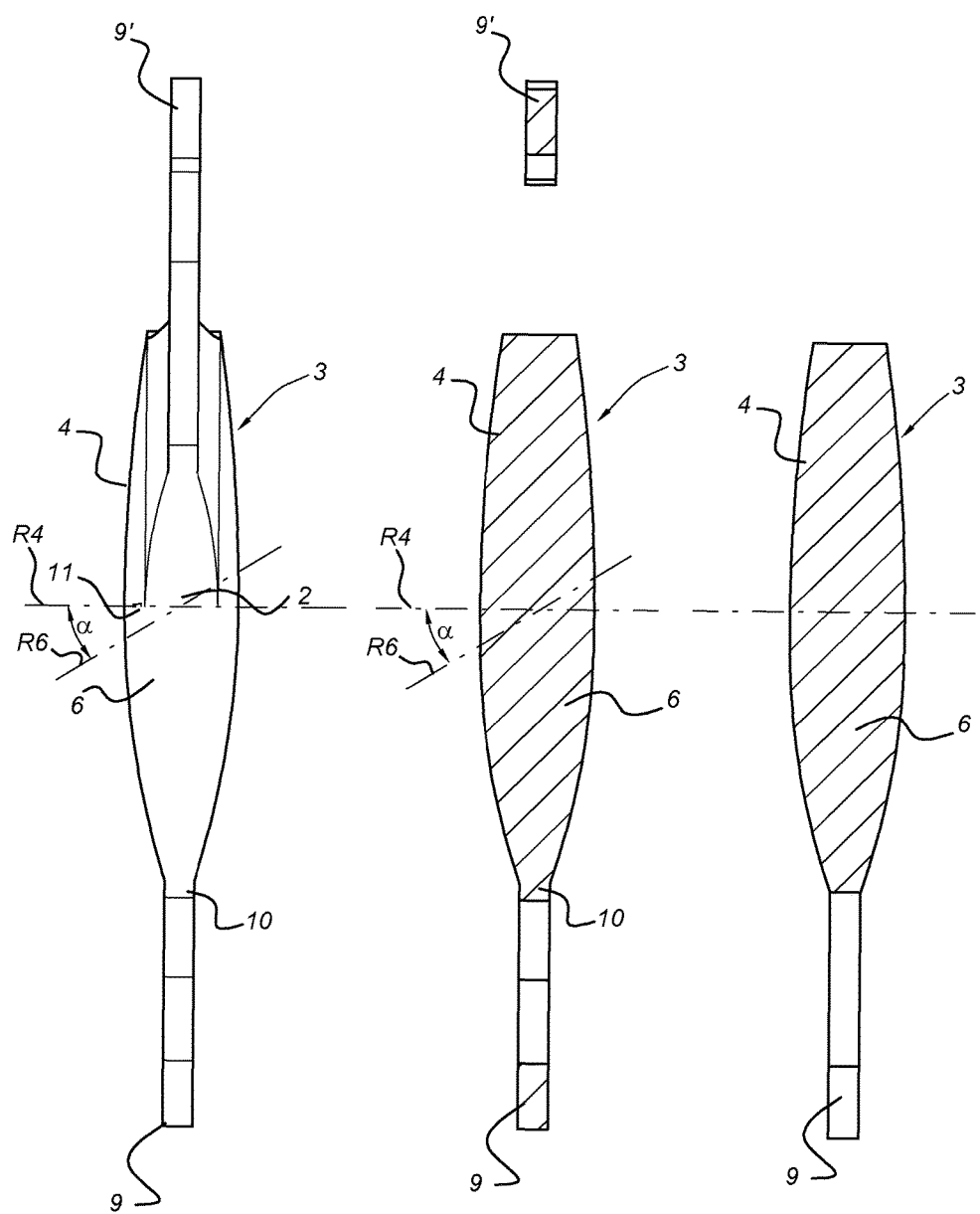

INTRAOCULAR LENS

FIELD OF THE INVENTION

The present invention relates to an intraocular lens comprising an optic, said optic comprising a first lens having a first optical axis for alignment with an optical axis of the human eye.

BACKGROUND OF THE INVENTION

Patients suffering from macula degeneration usually have impaired central visual fields and often rely heavily on peripheral vision, i.e. vision provided by the peripheral retina around the center of the macula, for daily tasks. Peripheral retina has low receptors (cons and rods) densities, which gives rise to a relatively poor resolution ability.

Such patients suffering from (age-related) macular degeneration are usually generally referred to as AMD patients. They often have compromised fovea at the center of the macula. However, there are still functional retina receptors surrounding the compromised receptors. These functional retina receptors are often peripherally located and have a larger spacing between each other. The increased spacing leads to decreased image resolution ability of the retina. For example, at 3 degrees nasal retina, the visual acuity is reduced to 0.4 compared to an 1.0 visual acuity at 0 degrees; at 5 degrees nasal retina, the visual acuity is reduced to 0.34 compared to the 1.0 visual acuity at 0 degrees.

There are three basic types of vision aids available conventionally for patients suffering from (age-related) macula degeneration, which can be applied either individually or in combination. A first type is a single telescope as the visual aid. Such telescopes are often mounted on spectacles, which are heavy and are not appealing cosmetically. Telescopes can also be implanted, which generally requires very large incisions during surgery to implant. The main disadvantage of using a telescope system alone is the resultant narrow visual field of view and overall poor image quality, which could cause a safety concern during normal daily activities.

A second type of vision aid is a prism. The prism is to realign the line of sight to the peripheral retina. This application needs to overcome a binocular fusion problem in order to avoid double imagery. The prism does not magnify the retinal images and therefore, the problem of low visual resolution due to the larger peripheral retina receptor spacing is not resolved.

A third type of vision aid is a magnifying glass, sometimes combined with a prism. This visual aid is often used as a desk-mounted device, which limits the application range for patients. A handheld version of this visual aid has vision instability and focus problems for patients with hand tremors.

Several alternatives have been developed and are based on "implantable optics". U.S. Pat. No. 4,759,761 discloses an intraocular lens which has interior mirrored surfaces forming a folded telescope of either the Gregorian type or the Cassegrain type.

US 2007/0276483 also discloses an intraocular telescopic lens formed by implantation of a negative lens and a positive lens with a spacer in between them.

US 2007/0182917 A1 discloses a diffractive multifocal lens, which in fact is an intraocular lens providing at least two powers of magnification. The optic has zone structures providing an added optical power over 6 dioptres in addition to a base optical power and is intended for use by AMD patients. Diffractive optics structures are inherently causing chromatic aberration and considerable halo's, glare and at loss of light energy of at least 20%, which reduces contrast sensitivity.

US 2009/0048671 discloses an intraocular implant with optical elements adapted to form images on the retina. It has at least one mirror operationally connected to the action of the ciliary muscle.

There are many types of intra ocular lenses that have been especially designed as an aid for patients which suffer from macular degeneration or which have another macula-related problem. All known designs have disadvantages, for instance, providing halo's, loss of light, or loss of visual resolution.

GB 2 468 367 A discloses adding a (second) intra-ocular lens in addition to the natural eye lens (or in addition to an intra-ocular lens replacing the natural eye lens). The (second) intra-ocular lens has its optical parallel but shifted with respect to the (intra-ocular lens replacing the) natural eye lens, and is arranged behind the (intra-ocular lens replacing the) natural eye lens along the optical axis of the (intra-ocular lens replacing the) natural eye lens. Both lenses therefore provide an imaging system that jointly project an image onto the macula of the eye such that the focal point is shifted away from the fovea. The imaging system of both lenses effectively only has one optical axis.

WO 2010/131955 A1 discloses an intra-ocular lens for replacing the natural eye lens. The intra-ocular lens comprises two optical elements which overlap along the optical axis to jointly project an image onto the macula of the eye. One of the optical elements can be shifted in a direction perpendicular to the optical axis, and optionally tilted, to tilt the optical axis and shift the image to a healthy sector of the macula.

U.S. Pat. No. 5,354,334 also discloses an intra-ocular lens for replacing the natural eye lens and comprising two optical elements which overlap along the optical axis to jointly project an image onto the macula of the eye. One of the optical elements can again be shifted in a direction perpendicular to the optical axis. The intra-ocular lens of the two optical elements disclosed in U.S. Pat. No. 5,354,334 and WO 2010/131955 A1 effectively only has one optical axis.

SUMMARY OF THE INVENTION

The invention aims to provide an intraocular lens for patients having macula problems.

Another or alternative object of the invention is to improve the visual field of view.

Another or alternative object of the invention is to provide patients experiencing macula degeneration with vision for orientation purposes and detailed vision.

Another or alternative object of the invention is to increase portability for application.

Another or alternative object of the invention is to increase the quality of vision, like a reduction of halo's.

Another or alternative object of the invention is increase the stability of the application.

According to a first aspect of the invention this is realized with an intraocular lens for insertion into a human eye having a macula, said intraocular lens comprising an optic, said optic comprising a first lens having a first optical axis arranged for alignment with an optical axis of the human eye; and a second lens having a second optical axis, wherein said second optical axis and said first optical axis enclose an angle between 0.5 and 10 degrees, the first lens and the second lens being arranged next to one another in a direction transverse to the first optical axis to provide no overlap in a direction along the first optical axis such that the first lens and the second lens each, independent from one another, image onto the macula of the eye.

Patients having such an intraocular lens will then have both vision available for orientation purposes and distance vision as provided by the first lens, and can further have detailed vision as provided by the second lens. The intraocular lens according to the invention does not suffer from the draw backs of known devices.

Preferably, said angle and a direction of said second optical axis are chosen such that said second lens images onto a functional part of the macula of the human eye, which functional part is not compromised by a defect, such as a scotoma.

Advantageously, the optic is a monolithic optic. A one-piece optic can be manufactured more efficiently and provides for a fixed position of first and second lenses with respect to one another.

Advantageously, said first lens is a main lens configured for distance vision, and has said second lens a second optical power magnifying relative to a first optical power of said first lens. Having the first lens configured as a main lens for distance vision is advantageous for orientation purposes. Preferably, said second optical power is selected such as to at least substantially alleviate a decrease in visual acuity resulting from imaging onto the peripheral retina of the human eye by having said second optical axis enclosing said angle with said first optical axis. Said second optical power may be larger than 4 dioptre, in an embodiment larger than 6 dioptre.

The reduced visual acuity of the peripheral retina is then compensated by the magnification of the second lens, providing the patient with a good detailed vision at reading distances.

Sight problems faced by patients with (age-related) macular degeneration (AMD) or low vision may use additional optical powers in reading glasses to help improve their seeing ability. Placing a strong additional optical power in a reading glass will provide a bigger magnified image, but results in fewer photons per receptor than would be the case if the same strong add power were placed in an intraocular lens. By placing a strong additional power into the intraocular lens, it will provide better contrast sensitivity for patients with AMD or low vision disorders than would be the case if the strong additional optical power is in the reading glass.

By placing the strong additional optical power into the intraocular lens, a larger photon per receptor concentration as compared to a strong additional optical power in the reading glass is achieved. It is found that the additional optical power of the lens implant preferably is larger than the current conventional level of 4 dioptres on the lens itself. Preferably, the additional optical powers should in the range of 5 to 10 dioptres, and potentially higher.

Some examples of conventional constructions include that of U.S. Pat. No. 5,217,489, which mentions that the near vision optical power is larger than the distance vision optical power by 2.0-5.0 dioptres and whose contents are incorporated herein by reference with respect to its bifocal intraocular lens structure.

U.S. Pat. No. 6,432,246 B1 reveals a type of multifocal lens known as progressive multifocal lens. Such a lens achieves power variations across the lens optic by changing the surface radius of curvature. This is based on the principle of geometric optics instead of the diffractive optics principle. The progressive multifocal lens has to deliver light over a wide range of foci and thus reduces the available light energy for individual focus. Therefore, it is not as effective as the diffractive optics multifocal IOL in this regard.

EP 2 219 065 A1 by Wanders et al reveals a type of multifocal lens known as refractive asymmetrical multifocal providing at least two powers of magnification that mentions that the near vision power is greater than the distance vision power by 1.0-5.0 dioptres and whose contents are incorporated herein by reference with respect to its bifocal intraocular lens structure.

Refractive multifocal lenses such as disclosed in U.S. Pat. No. 5,217,489 can be changed upon higher add power and improved light energy concentration at distance focus and near focus, as anticipated by the inventor. The present invention has bifocal or multifocal lenses with distinct foci that is refractive but not utilizing multifocal lens in the manner of EP 2 219 065 A1.

For patients who had macular translocation surgeries, their normal line of sight are no longer aligned with their macula. Consequently, the macular translocation treated eye could show the undesirable "tropia" appearances such as esotropia or exotropia. Further, if patients had their both eyes treated with macular translocation surgeries, there could be negative impact to the intended vision function. For example, if the left eye needs to look up to see better, and the right eye needs to look down to see better, then such patients cannot function well because such binocular eye movements are very difficult. This embodiment of redirecting the retinal image location can reduce or correct the "tropia" appearances by relocating the light of sight to the new macular location.

BRIEF DESCRIPTION OF THE DRAWINGS

Embodiments of the invention will be described with reference to the drawings, in which identical or like reference numerals refer to identical or like parts, and in which

FIG. 19 shows a side view on the embodiment of FIG. 15;

FIG. 20 shows a cross-section of the embodiment of FIG. 15 along the line III-III in FIG. 18;

FIG. 21 shows a cross-section of the embodiment of FIG. 15 along the line IV-IV in FIG. 18.

DETAILED DESCRIPTION OF EMBODIMENTS

Figure 1:
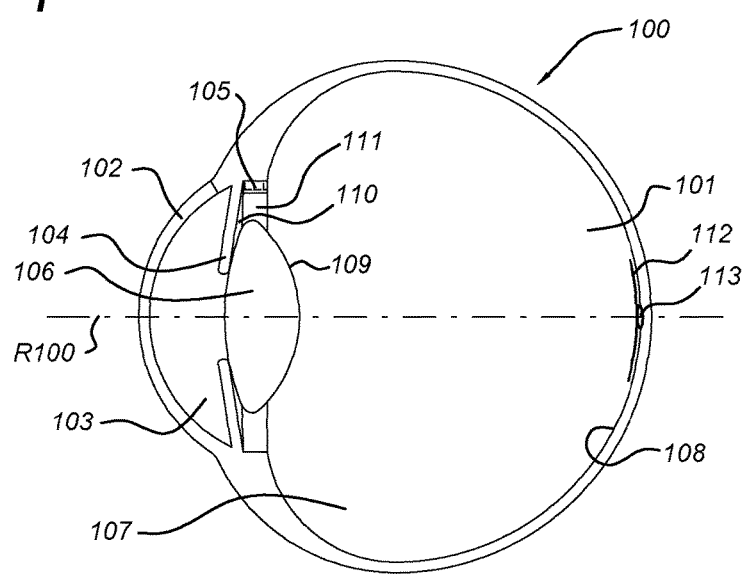
FIG. 1 shows a cross-section of the human eye.

A schematic view of a human eye 100 with its natural lens 106 inside lens capsule or capsular bag 109 is shown in FIG. 1. The eye has a vitreous body 101 within posterior chamber 107. Retina 108 is on the inside of the posterior chamber 107, which further comprises macula 112 with fovea 113 at the centre thereof. The macula contains the photoreceptor cells, the fovea predominantly having cone photoreceptor cells although it does not have a sharply defined boundary. It merely shows a gradual transition from an area having a high density of (cone) photoreceptor cells to a peripheral area that predominantly has rod photoreceptor cells at decreasing density going from the center of the macula outwards. An optical axis R100 of eye 100 passes through the centre of iris 104 and the center of macula 112 and fovea 113. The eye further has a cornea 102 and an anterior chamber 103. The lens 106 and capsular bag 109 are held by ciliary muscle 105 and zonule fibres or ciliary zonules 111. The (ciliary) sulcus 110 is in between iris 104 and ciliary zonules 111.

Figure 2:
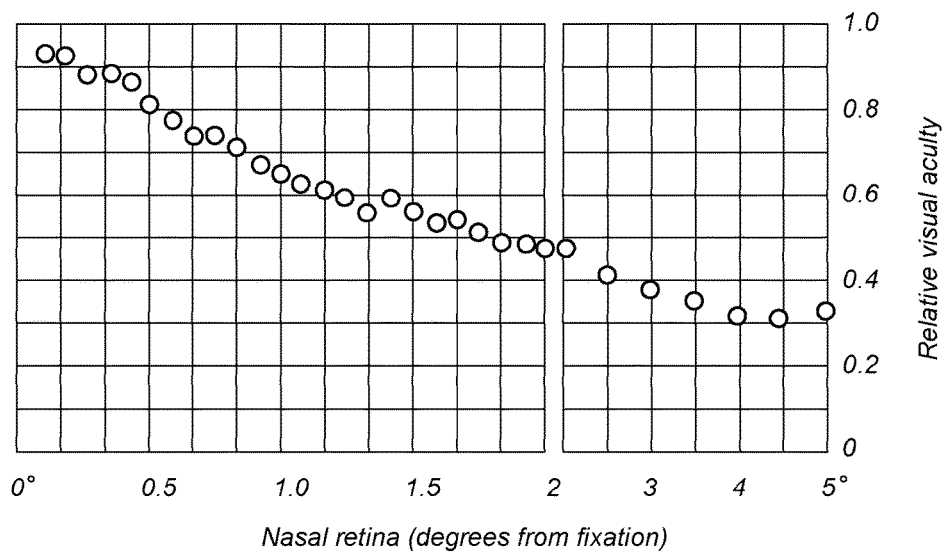
FIG. 2 shows a graph (taken from "Clinical Visual Optics", Bennett and Rabbetts, page 37, Butterworth, Boston, 1984) displaying the peripheral relative visual acuity of the nasal retina as a function of the angular position from the center of the macula (fovea)

The center of the macula predominantly provides resolution but it is known that peripheral vision can still provide adequate resolution. FIG. 2 shows that the resolution is progressively reduced in the nasal retina going from the center of the macula in the nasal direction, which is from the center of the macula in the direction of the human's nose. Temporal, superior and inferior peripheral retinas are expected to have similar behaviour at a similar small degree off-axis range. Visual acuity is reduced from 1.0 at the center of the macula to 0.5, 0.4 and 0.34 at 2, 3 and 5 degrees nasally, respectively. Accordingly, increasing or magnifying retina image size relative to the image size associated with about 36 centimeter reading distance could allow the peripheral retina to effectively resolve small text and objects comparable to what normal eyes can do using the central retina (being central macula and central fovea). The magnification could be a factor 2.0 at 2 degrees peripheral retina, a factor 2.5 at 3 degrees peripheral retina, or a factor 3.0 at 5 degrees peripheral retina taking the above visual acuity values as a basis.

Macular degeneration generally occurs at the macular central region, although it may occur at another location in the macula. To improve vision of a person suffering from the (age-related) macular degeneration and having a scotoma, imaging can be done on another part of the macula, which has not been compromised by macula degeneration. Such parts are referred to as functional retina.

Figure 3:
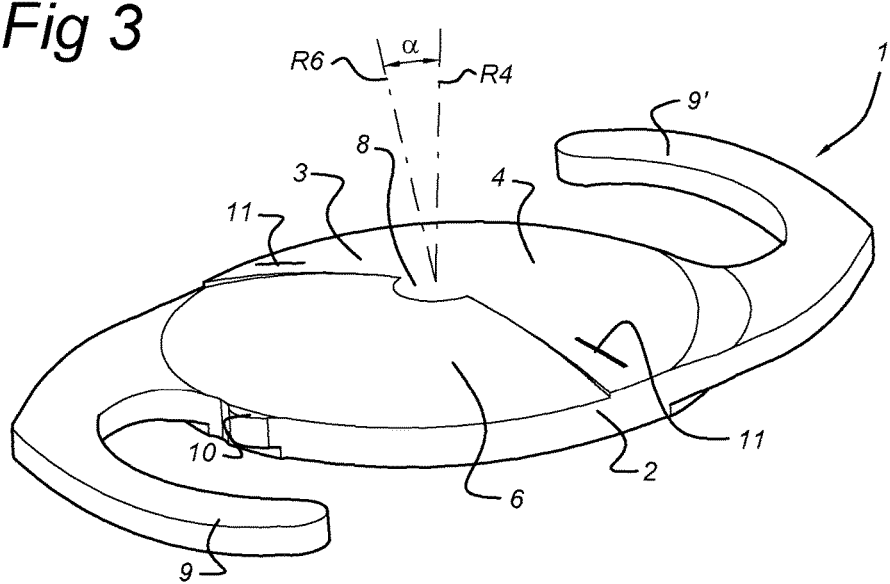
FIG. 3 shows a perspective view on an anterior side or front side (for facing away from the retina of the eye) of a first embodiment of an intraocular lens according to the invention.
Figure 4:
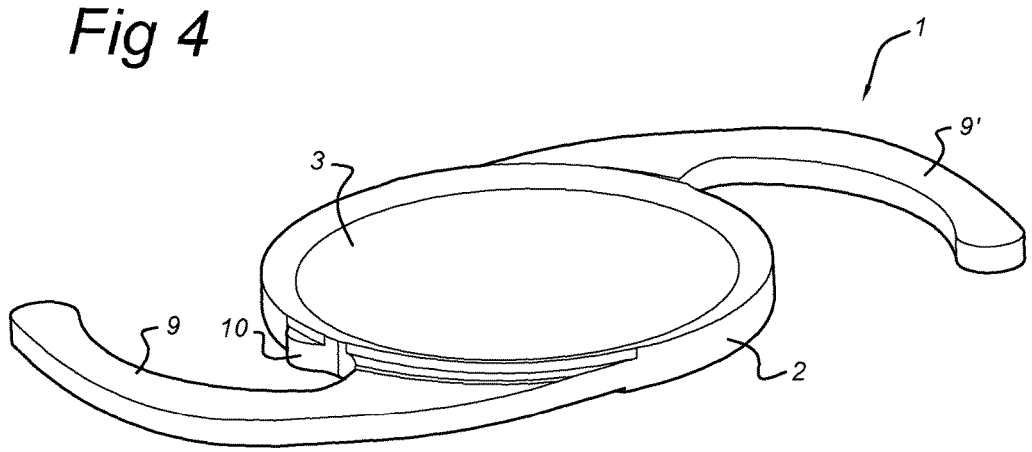
FIG. 4 shows a perspective view on a posterior side or back side (for facing towards the retina of the eye) of the first embodiment.
Figure 5:
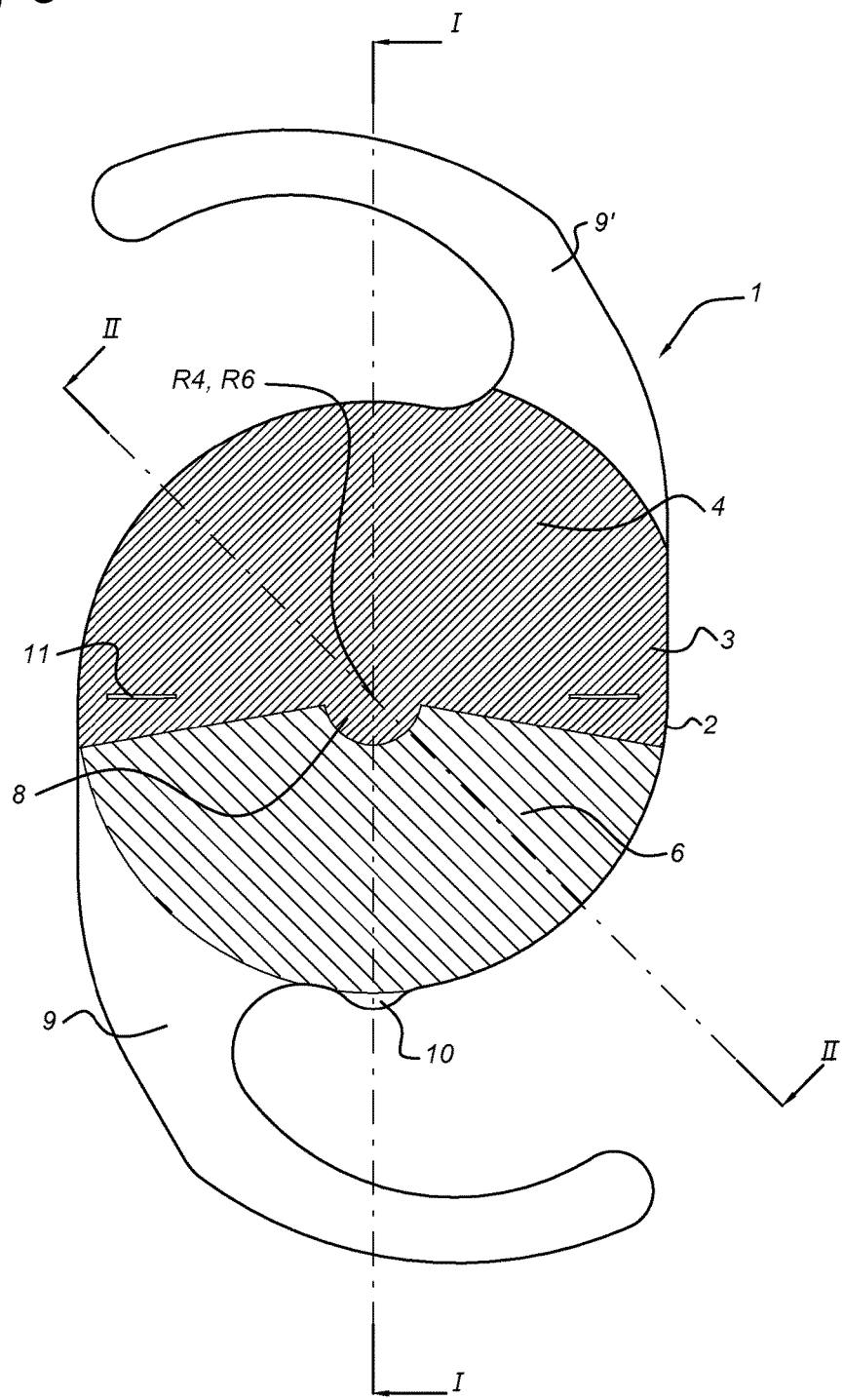
FIG. 5 shows a front view on the first embodiment.
Figure 6:
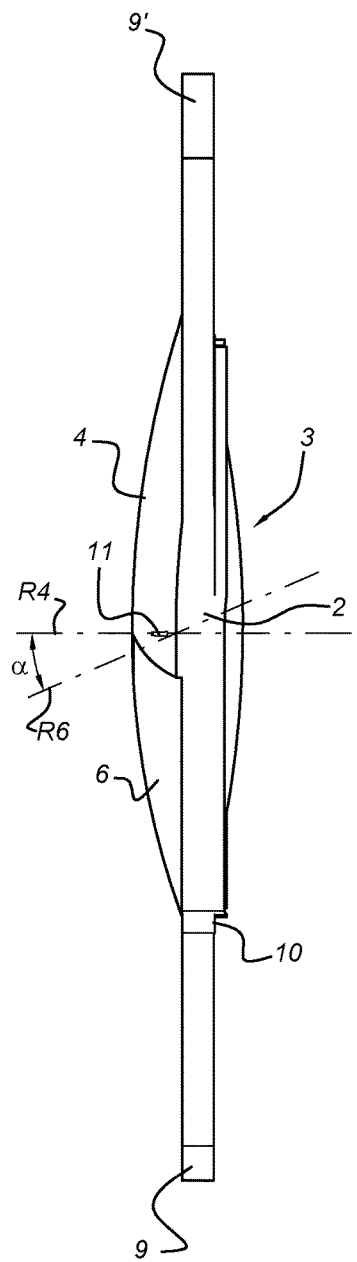
FIG. 6 shows a side view on the first embodiment.
Figure 7:
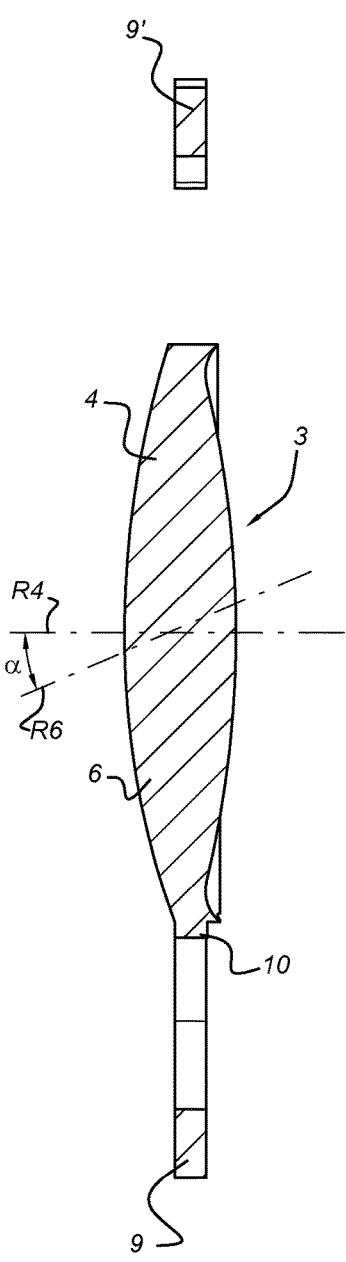
FIG. 7 shows a cross-section of the first embodiment along the line I-I in FIG. 5.
Figure 8:
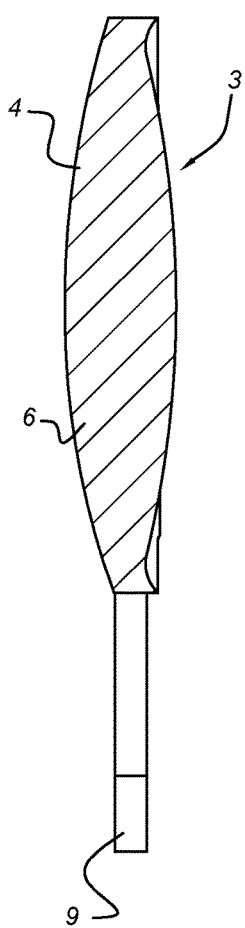
FIG. 8 shows a cross-section of the first embodiment along the line II-II in FIG. 5.

The present invention provides an intraocular lens 1 of which an embodiment is shown in FIGS. 3-8 for that purpose. Intraocular lens 1 comprises so-called haptics 9, 9' and an optic 3 having a circumference 2. The haptics are intended for fixation purposes of the intraocular lens within the human eye. Optic 3 comprises a first lens 4 and a second lens 6. Both lenses 4, 6 will generally have a different optical power. Lens 4 has an optical axis R4 and lens 6 has an optical axis R6. FIGS. 3 and 5 further show that optic 3 has a central lens part 8. Alignment markers 10, 11 present on the intraocular lens can be used by the surgeon for correct positioning of the intraocular lens in the human eye during surgical implantation.

Figure 9:
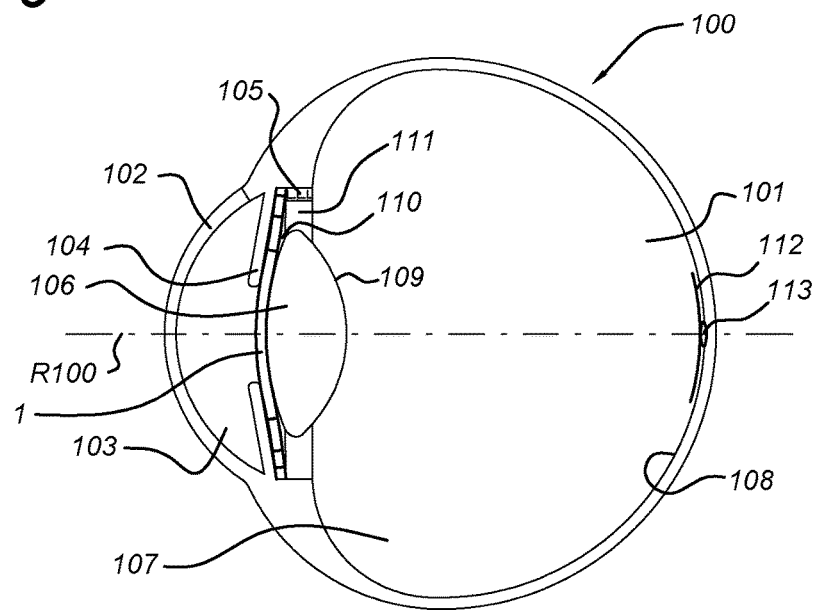
FIG. 9 shows a cross-section of the human eye with an intraocular lens according to the invention inserted in the sulcus.
Figure 10:
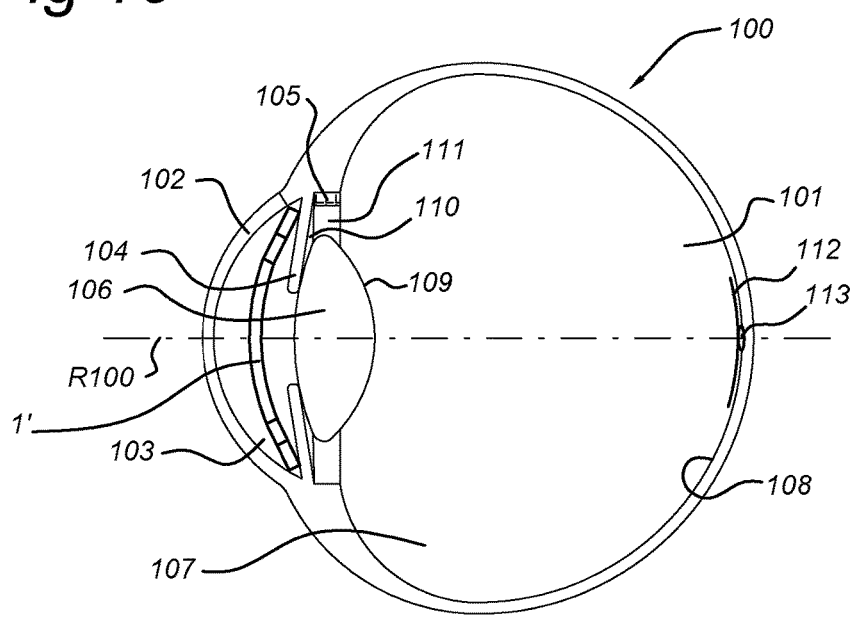
FIG. 10 shows a cross-section of the human eye with an intraocular lens according to the invention inserted in the anterior chamber of the eye.
Figure 11:
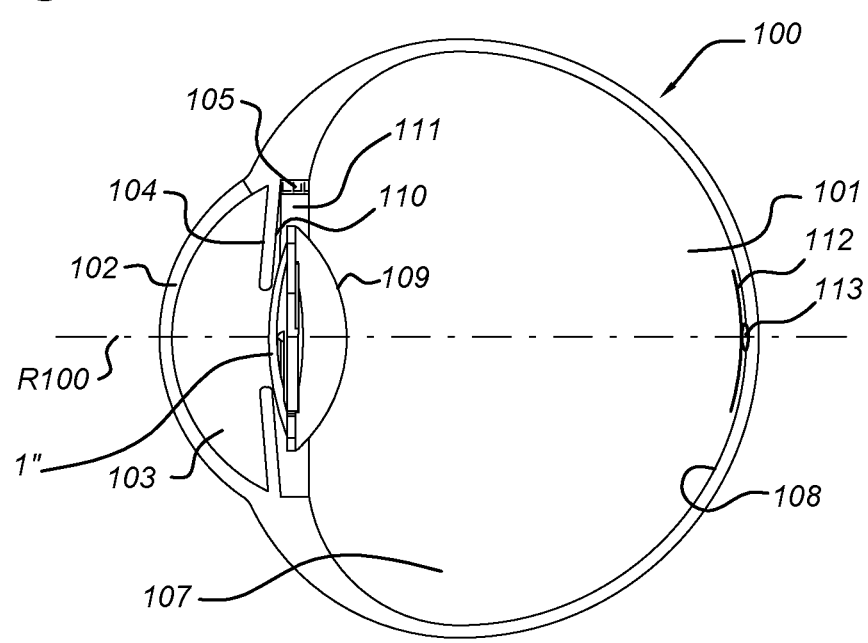
FIG. 11 shows a cross-section of the human eye with an intraocular lens according to the invention replacing the natural eye lens in the capsular bag.

FIGS. 9-11 show an intraocular lens 1 according to the invention provided in a human eye 100. FIG. 9 shows the intraocular lens 1 positioned in the sulcus 110 between iris 104 and capsular bag 109, FIG. 10 shows intraocular lens 1' positioned in the anterior chamber 103, and FIG. 11 shows intraocular lens 1" positioned in the capsular bag 109 as a replacement for the natural lens. The intraocular lens 1, 1' as shown in FIGS. 9 and 10 will be in addition to the natural eye lens or an intraocular lens 1" already provided in capsular bag 109.

Lens 4 of optic 3 of the intraocular lens is, in the embodiment shown, a main lens having its optical axis R4 aligned with the optical axis R100 of the human eye when positioned in the human eye. Main lens 4 will generally be optimized for distance vision and an image will be projected around the center of the macula, which allows the person concerned a broad visual field for, inter alia, orientation. Main lens 4 may provide optical correction for any imaging errors in the human eye. However, it may also be (non-imaging) part having no optical power in case such optical correction is not required or not desired.

Lens 6 is optimized for near vision for providing the person concerned the ability to distinguish detail, for instance, for reading purposes. Imaging on the scotoma, that is generally present in the center of the macula, is avoided by having optical axis R6 of lens 6 tilted with respect to optical axis R4 of main lens 4, and thus tilted with respect to optical axis R100 of the human eye when the intraocular lens is provided in the human eye. A detailed image will therefore be projected next to the scotoma, allowing the retina to distinguish detail with the most sensitive part of the functional retina which has not been compromised.

Figure 12:
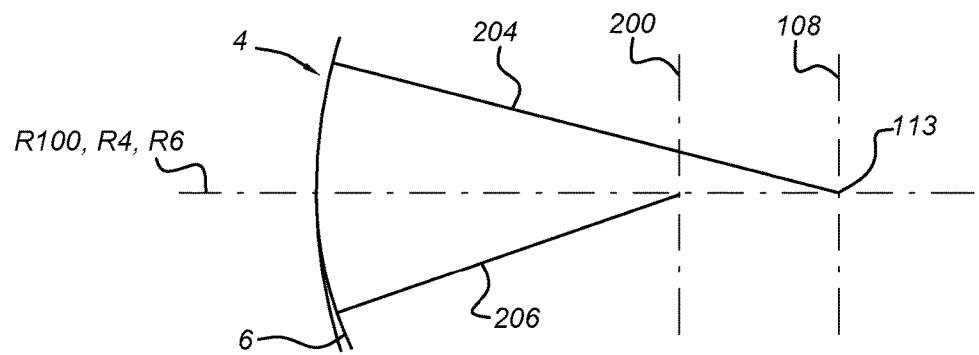
FIG. 12 schematically shows the optical system of the human eye with an intraocular lens inserted, and having the optical axis of the human eye coinciding with the optical axis of the intraocular lens.
Figure 13:
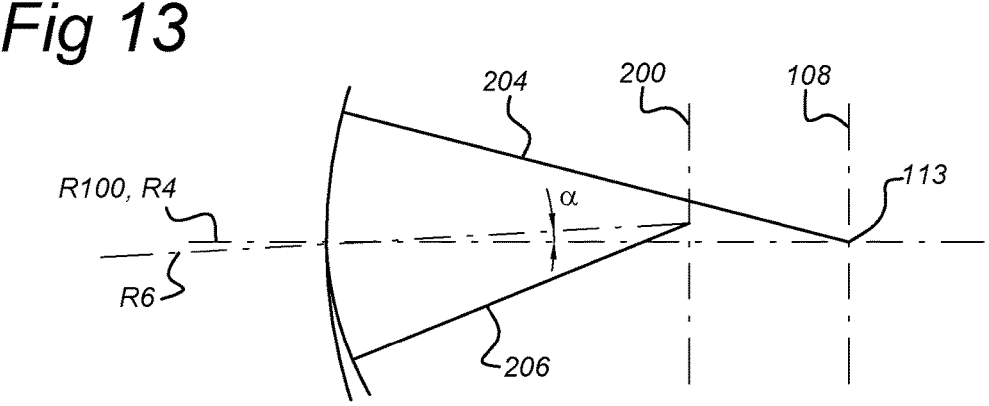
FIGS. 13 and 14 schematically show the optical system of the human eye with an intraocular lens inserted, and having the optical axis of the human eye enclosing an angle with the optical axis of the intraocular lens.
Figure 14:
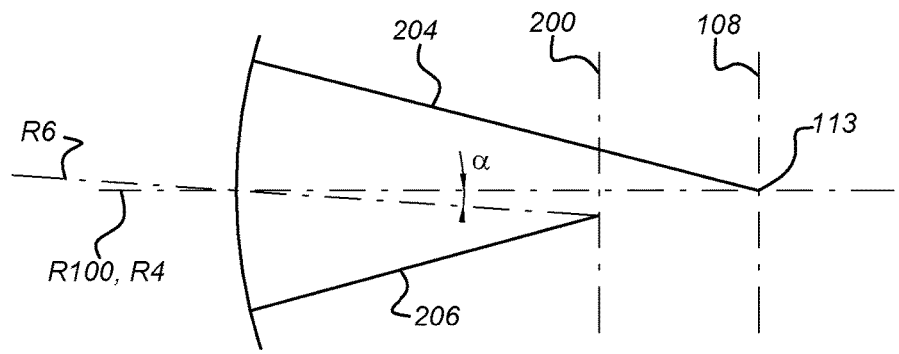
Figure 15:
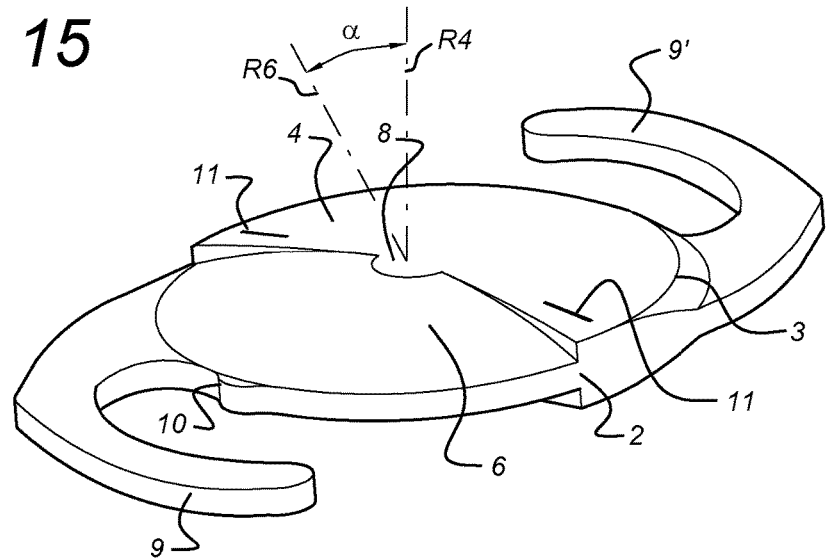
FIG. 15 shows a perspective view on an anterior side or front side (for facing away from the retina of the eye) of another embodiment of an intraocular lens according to the invention.
Figure 16:
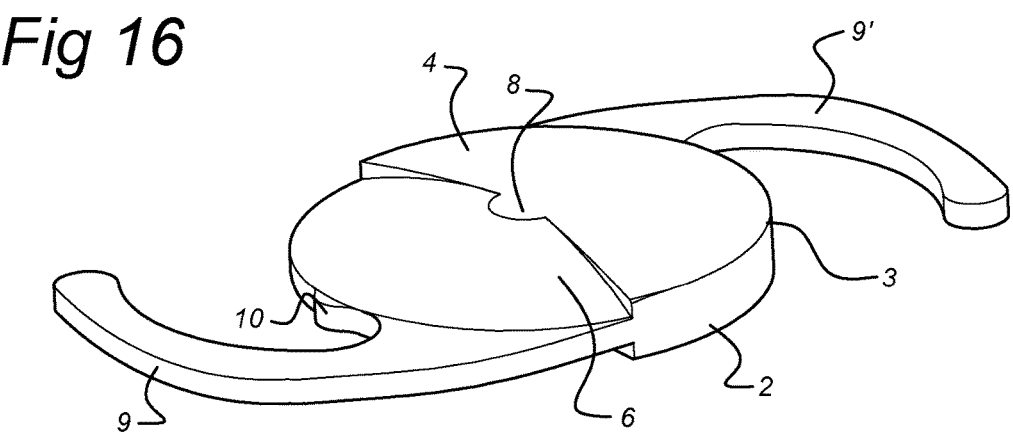
FIG. 16 shows a perspective view on a posterior side or back side (for facing towards the retina of the eye) of the embodiment of FIG. 15.
Figure 17:
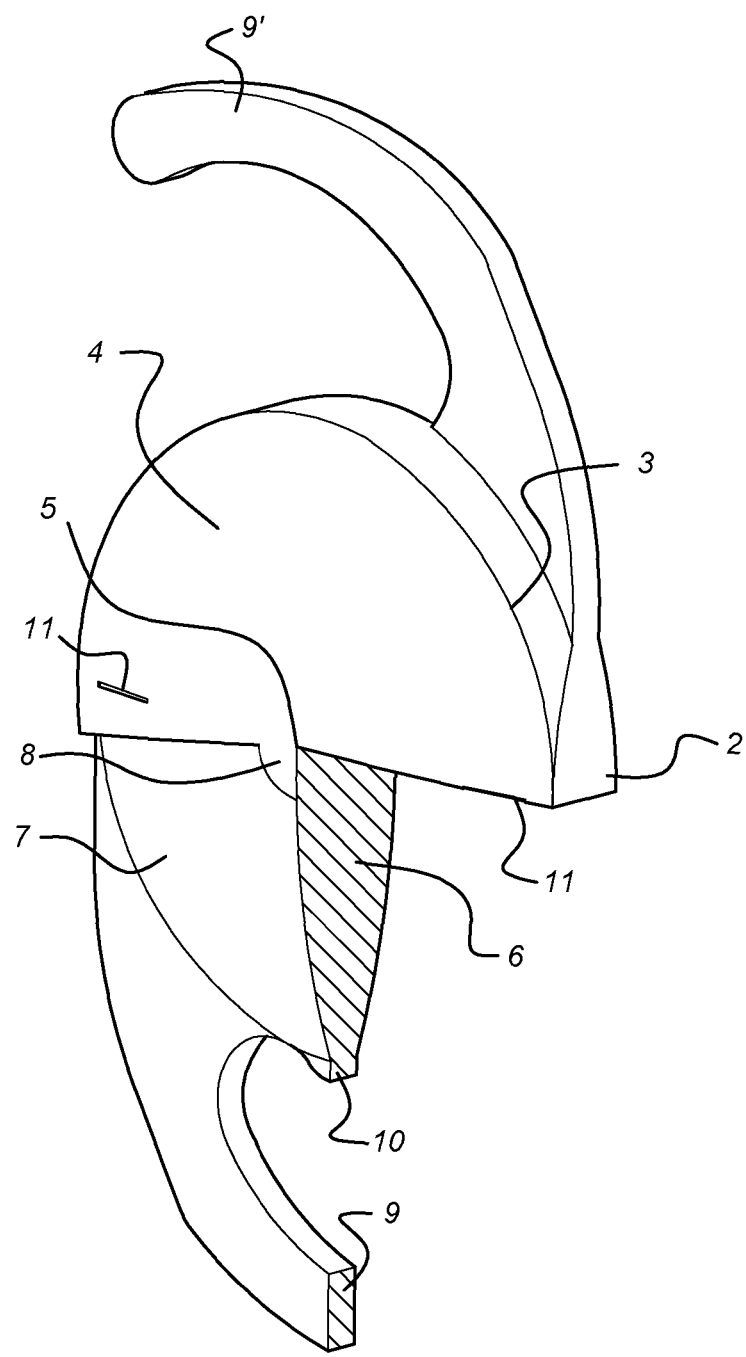
FIG. 17 shows the view of FIG. 15 partially in cross-section.
Figure 18:
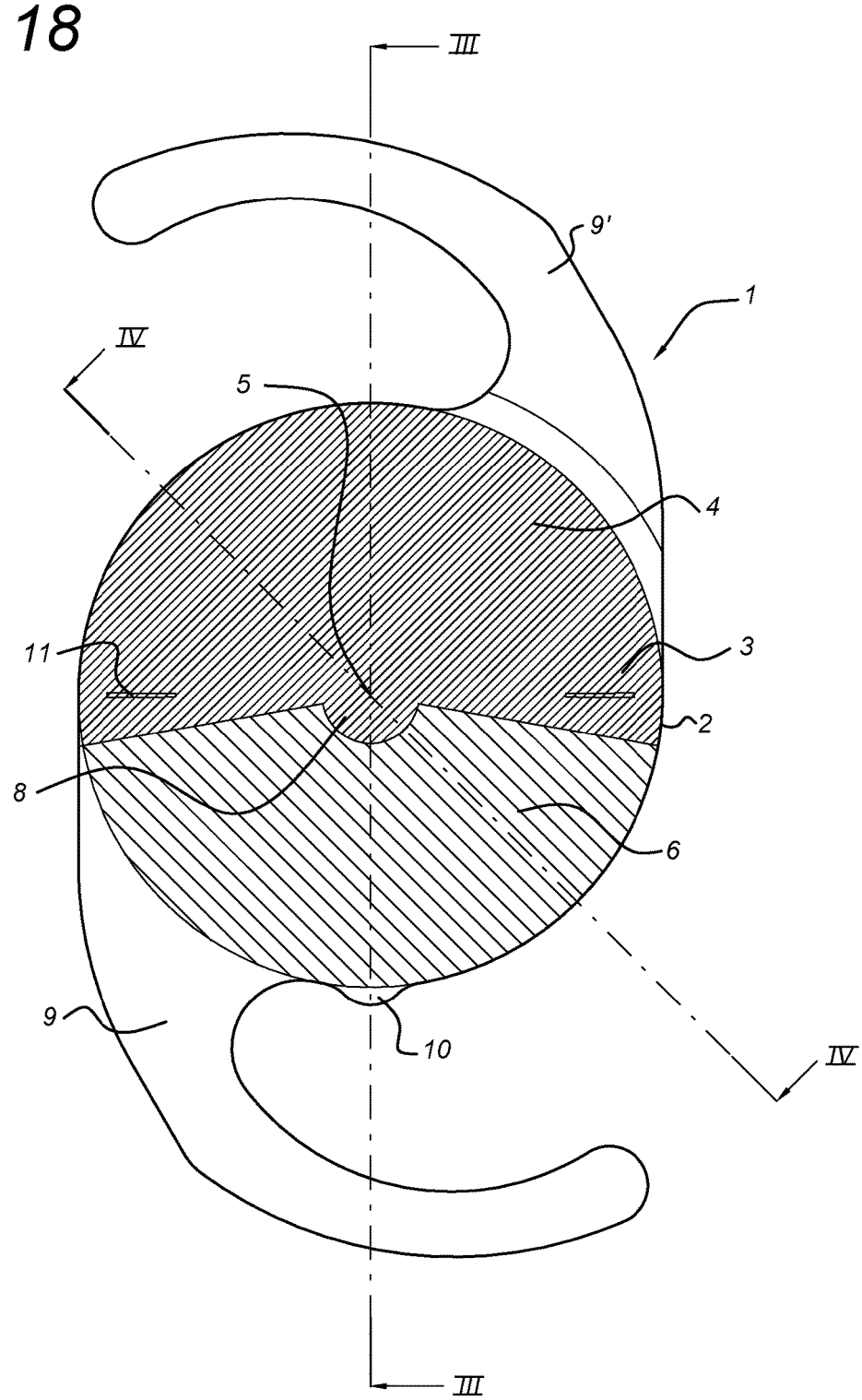
FIG. 18 shows a front view on the embodiment of FIG. 15.

FIGS. 12-14 schematically show the optical system of human eye with the intraocular lens present. An image from distance vision will be projected through main lens 4 on retina 108 around the center of the macula and fovea 113. Lens 6 only provides a sharp image of distance vision in a plane 200 in front of retina 108, not a sharp image of distance vision on retina 108 itself. In case of imaging an object much closer to the eye, the imaging plane 200 for that object will shift towards retina 108 and coincide with the retina when the object is close enough to the human eye. Then a sharp image of that object is projected on retina 108.

The situation for a regular intraocular lens having both optical axes R4 and R6 coincide with optical axis R100 of the human eye is shown in FIG. 12. In this situation near vision will be imaged around the center of fovea 113. In case a scotoma is present in the center of fovea 113, near vision will be imaged onto the scotoma. Such near vision can therefore not be "seen" since the scotoma provides an area of the retina that has no optical detection capability.

FIGS. 13 and 14 show optical axis R6 tilted with respect to optical axis R4, and therefore with respect to optical axis R100. Near vision is in these situations imaged next to the center of fovea 113 avoiding a scotoma present in that location and the image of near vision can therefore be "seen" by the person concerned.

Bifocal and multifocal optics are known in the ophthalmic optics field, but optical axes of the known bifocal or multifocal optics are aligned. Further, existing ophthalmic bifocal or multifocal optics have additional optical power (in addition to a base optical power) optimized for reading at 35 centimetre. The highest multifocal intraocular leans (IOL) nowadays has about 4 dioptre additional optical power, which is for a reading distance of about 36 cm from the human eye. Using an optical model for the human eye one can derive table 1, taking the image size at a reading distance of 36 cm as a reference (relative image size at 36 cm reading distance equal to 1.0). To arrive at the values of table 1 a value of 43 dioptre for the cornea and a value of 18 dioptre for the eye lens have been taken, but these values may vary from person to person.

Table 1 shows that with a 4.3 dioptre additional power the relative magnification is about a factor 1.2. A factor 1.2 magnification is likely not to be adequate for (age-related) macular degeneration. FIG. 2 shows that a factor 1.2 magnification is only useful if the 0.5 degrees retina is not damaged by macular degeneration, since the visual acuity at 0.5 degrees is about 0.8 as shown in FIG. 2 (1.2 magnification×0.8 relative visual acuity=0.96). A preferred magnification is chosen such that it about compensates for a loss in visual acuity relative to the center of the macula. This would compensate for both a loss in resolution and a loss light being detected since the density of photo receptors decreases in a direction away from the center of the macula.

An angle α of 1 to 2 degrees between optical axes R6 and R4 proves mostly sufficient and would require a magnification of about a factor 2, as can be deduced from the reduction in relative visual acuity shown in FIG. 2. Table 1 shows that such magnification introduces a reading distance of about 20 centimetres, which is still quite practical. An angle α of 5 degrees would require a magnification of about a factor 3, and introduces a reading distance of about 13 to 14 centimetres. An angle α in the range of 0 to 6 degrees is most practical, although one could go to even larger angles α in some situations.

TABEL 1

Relation between reading distance, intraocular lens (IOL) additional optical power for near (reading) vision and relative image size change.

| Reading distance (cm) | Additional IOL near power with respect to optical power for distance vision (dioptre) | Relative image size change relative to 36 cm reading distance |
|---|---|---|
| 36.4 | 3.8 | 1.0 |
| 30.8 | 4.3 | 1.2 |
| 25.0 | 5.0 | 1.5 |
| 20.0 | 6.0 | 1.9 |
| 16.0 | 7.3 | 2.5 |
| 13.8 | 8.3 | 3.0 |
| 12.5 | 9.0 | 3.3 |

FIGS. 15-21 show another embodiment of an intraocular lens according to the invention, which is especially suited for having a lens 6 with a very high additional optical power relative to lens 4. All parts indicated in the embodiment are similar to the ones shown in the embodiment of FIGS. 3-8. A very high additional optical power of lens 6 requires a high curvature, which would result in a partially thin and therefore unstable optic 3. The overall thickness of optic 3 and lens 4 is taken relatively high to allow for the high curvature of lens 6. The relatively high thickness of lens 4 is well visible in the figures as compared to the embodiment shown in FIGS. 3-8, making the least thick part in the area close to alignment marker 10 of about comparable thickness to the thickness of the embodiment shown in FIGS. 3-8 in the area close to the alignment marker 10.

The additional optical power of lens 6 may be provided on one side of optic 3, as is shown for the embodiment of FIGS. 3-8, which may give rise to extremely high curvatures. The embodiment of FIGS. 15-21 shows the additional optical power of lens 6 provided on both the anterior and posterior sides of optic 3.

The optical active surfaces of the first and second lenses can be provided on one or both of the anterior and posterior surfaces of optic 3. The anterior surfaces faces away from the retina and towards the cornea. The posterior surface faces towards the retina. When positioned in the sulcus 110 or anterior chamber 103, the anterior surface of the intraocular lens 1, 1' will generally be convex, while the posterior surface will generally be concave.

Figure 22A:
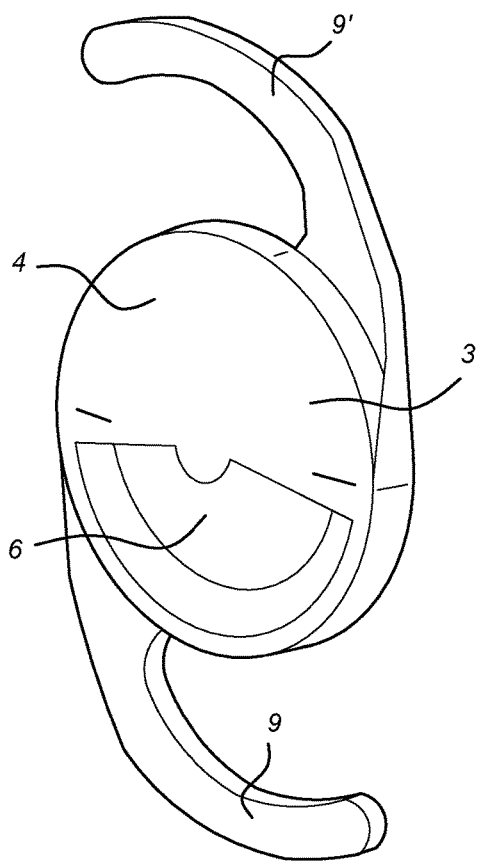
FIGS. 22a and 22b show perspective views on the anterior and posterior sides, respectively, of a slightly different alternative of the embodiment shown in FIGS. 15-21.
Figure 22B:
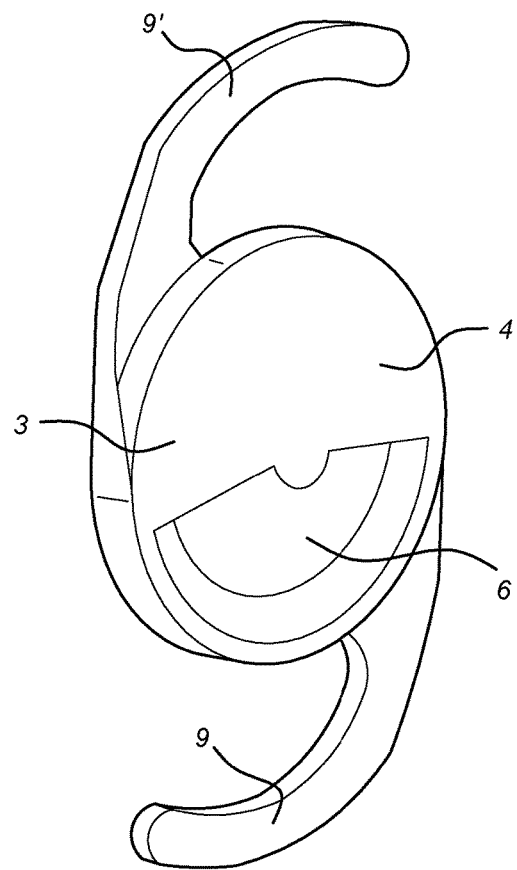

FIGS. 22a and 22b show perspective views on the anterior and posterior sides of a slightly different alternative to the embodiment of FIGS. 15-21. It clearly shows that lens 6 is provided as a recessed part within optic 3 and lens 4. The boundaries of the recessed part may have a shape as disclosed in WO 2010/095938 A1, which is incorporated herein by reference. Lens 6 of the embodiment of FIGS. 3-8 may also be provided as a recessed part within optic 3 and lens 4.

Below a few examples are given for some populations of people having developed (age-related) macular degeneration. A first population concerns persons that already have or could benefit from an intraocular lens. A bifocal or multifocal intraocular lens (IOL) 1 on a sulcus fixed IOL carrier as shown in FIG. 9 can be used. The optical power is about 0 dioptre (plano or near plano) for the emmotropic patient's distance vision and normal visual field size. The additional optical power for near vision will allow the patient to read or focus at a short distance, of e.g. 12 to 18 cm, so that the retinal image size of the normal reading text is resolvable by a good retinal receptor array. As a placement alternative, this bifocal or multifocal can also be provided on an anterior chamber IOL carrier and put into the anterior chamber of the eye. A second population concerns non-cataract presbyobic patients that have developed (age-related) macular degeneration. For such persons a bifocal or multifocal IOL 1" in a capsular bag can be used, as shown in FIG. 11. The optical power for distance vision is selected for the patient's distance vision needs and normal visual field size. The optical power for near vision will allow the patient to read or focus at a short distance, of e.g. 12 to 18 cm, so that the retinal image size of the normal reading text is resolvable by the good retinal receptor array.

A third population concerns non-cataract non-presbyopic patients that have developed (age-related) macular degeneration or low vision patients (amblyopic population). For this population it can be envisioned to use a bifocal or multifocal IOL 1 or 1' in an anterior chamber or sulcus fixed IOL carrier, as is shown in FIGS. 10 and 9, respectively, in addition to an IOL1' in the capsular bag, as shown in FIG. 11. The multilens/multifocal system has at least one telescopic view system (e.g. IOL 1 or 1') together with a non-telescopic view system (e.g. IOL 1"). The telescopic system provides magnified retina image for visual acuity improvement. The non-telescopic view system provides the normal visual field of view. In cases that the natural accommodation of the natural crystalline lens is to be preserved, a different embodiment can be used in which the natural crystalline lens will be kept to work with a bifocal/multifocal IOL in an anterior chamber or sulcus fixed IOL carrier. In such cases the magnified retinal images are provided via the higher add power of the bifocal/multifocal IOL. One can also envision to have both the telescopic view system and non-telescopic view system combined in one IOL carrier 1".

Any other cross application of the three approach examples to any of the three populations may be employed. Also, other forms of IOL lens carrier for the bifocal/multifocal IOL such as iris fixated IOL carriers, is envisioned. This visual aid device could also be used together with commercially available (age-related) macular degeneration drugs and/or contact lenses and refractive ablations. The drug will steady and stabilize the vision to help the device improve the patient vision and the surgery or device can help to improve the patient's vision.

The present invention addresses the need to keep a larger visual field of view than that provided by the three basic types of vision aids available conventionally as previously discussed by using bifocal or multifocal optics. The present invention also addresses the need for an increase in portability for application and for an improvement in cosmetics over such conventionally basic types and by implementing the optics inside the eye in a conventional minimally invasive surgical procedure, unlike implanted telescopes.

The inventive bifocal or multifocal device or IOL provides at least two focusing powers. Patients' normal wide visual field needs are met by the distance power of the device. Patients' reading needs are met by allowing the patients to see focused images at a closer sight distance.

Once the image size is magnified enough, the corresponding focus power or imaging capability will bring a focused clear image to the retina. Normal eye optics do not provide imaging capability for bringing a focused clear image to retina at such close distance except in very young children eyes.

While the accurate calculation could be done through ray tracing, the above approximation should illustrate the concept. With the present inventive device, (age-related) macular degeneration patients could have normal visual field of view during motion except with a central Scotoma. When they need to read text, reading ability is triggered by bringing the text close to get a clearly focused image. Treated patients can read texts in the very small Times New Roman of N4 or N5 at 20 to 12 cm using the retina adjacent to the fovea (depending on their Scotoma size).

Therefore, the invention modifies bifocal and multifocal optics to provide a relatively large additional optical power in the IOL plane. The preferred additional optical power is larger than +6 dioptres depending on reading distance needs, although any larger optical power, such as 8 dioptres, 9 dioptres or 10 dioptres, is envisioned. The additional optical power is taken as the difference between the near vision optical power and the distance vision optical power of the bifocal or multifocal IOL.

The surfaces of the second lens can also be provided with diffractive optical elements for providing additional optical power. The required optical can then be distributed over a refractive part and a diffractive part of the second lens. Such a configuration would even provide a trifocal lens: a first optical power provided by the first lens, a second optical power provided by only the refractive part of the second lens, and a third optical power provided by the addition of the refractive and diffractive optical power of the second lens. A diffractive optical structure that may be used is, for instance, disclosed with reference to FIGS. 12 to 16 in WO 2010/095938, which is incorporated herein by reference, in which the diffractive pattern is superimposed on a convex or concave surface. Such a diffractive pattern is further disclosed in EP 0 888 564 and EP 1 194 797, which are incorporated herein by reference.

To treat patients with (age-related) macular degeneration (AMD), any of the embodiments disclosed may be used in conjunction with administration of an AMD drug to stop further development of AMD. The AMD drug may be an ophthalmic pharmaceutical preparation for the treatment of advanced macular degeneration.

It will also be clear that the above description and drawings are included to illustrate some embodiments of the invention, and not to limit the scope of protection. Starting from this disclosure, many more embodiments will be evident to a skilled person which are within the scope of protection and the essence of this invention and which are obvious combinations of prior art techniques and the description.

The invention claimed is:

1. An intraocular lens (1) for insertion into a human eye (100) having a macula (112), said intraocular lens (1) comprising an optic (3), said optic comprising:
    a first lens (4) having a first optical axis (R4) arranged for alignment with an optical axis (R100) of the human eye (100); and
    a second lens (6) having a second optical axis (R6), wherein said second optical axis (R6) and said first optical axis (R4) intersect each other at an intersection, wherein at the intersection, said second optical axis (R6) and said first optical axis (R4) enclose an angle (α) limited to a range between 0.5 and 10 degrees,
    the first lens (4) and the second lens (6) being arranged next to one another in a direction transverse to the first optical axis (R4) to provide no overlap in a direction along the first optical axis (R4) such that the first lens (4) and the second lens (6) each, independent from one another, image onto the macula (112) of the eye (100).

2. The intraocular lens according to claim 1, wherein said angle (α) and a direction of said second optical axis (R6) are chosen such that said second lens (6) images onto a functional part of the macula (112) of the human eye (100), which functional part is not compromised by a defect, such as a scotoma.

3. The intraocular lens according to claim 2, wherein said optic is a monolithic optic.

4. The intraocular lens according to claim 1, wherein said optic is a monolithic optic.

5. The intraocular lens according claim 1, wherein said angle (α) is between 0 and 6 degrees.

6. The intraocular lens according to claim 1, wherein said first lens (4) is a main lens configured for distance vision, and said second lens (6) has a second optical power magnifying relative to a first optical power of said first lens (4).

7. The intraocular lens according to claim 6, wherein said second optical power is larger than 4 dioptre.

8. The intraocular lens according to claim 7, wherein said second optical power is larger than 6 dioptre.

9. The intraocular lens according to claim 1, wherein said second optical power is selected such as to at least substantially alleviate a decrease in visual acuity resulting from imaging onto the peripheral retina of the human eye (100) by having said second optical axis (R6) enclosing said angle with said first optical axis (R4).

10. The intraocular lens according to claim 9, wherein said second optical power is larger than 4 dioptre.

11. The intraocular lens according to claim 1, wherein a surface of said second lens (6) is recessed relative to a surface of said first lens (4).

12. The intraocular lens according to claim 1, wherein said optic (3) comprises an anterior surface for facing away from the retina of the human eye (100), said anterior surface comprising a first anterior surface section being a surface of said first lens (4) and a second anterior surface section being a surface of said second lens (6).

13. The intraocular lens according to claim 12, wherein said second anterior surface section is recessed relative to the first anterior surface section.

14. The intraocular lens according to claim 1, wherein said optic (3) comprises a posterior surface for facing towards to the retina of the human eye (100), said posterior surface comprising a first posterior surface section being a surface of said first lens (4) and a second posterior surface section being a surface of said second lens (6).

15. The intraocular lens according to claim 14, wherein said second posterior surface section is recessed relative to the first posterior surface section.

16. The intraocular lens according to claim 1, wherein said second lens is provided with a diffractive structure for providing a diffractive optical power in addition to a refractive optical power of the second lens.

* * * * *